US010774022B2

(12) United States Patent
Sun et al.

(10) Patent No.: US 10,774,022 B2
(45) Date of Patent: *Sep. 15, 2020

(54) PROCESS FOR MAKING BIOBASED FUEL ADDITIVES

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 1151 days.

This patent is subject to a terminal disclaimer.

(21) Appl. No.: 14/683,187

(22) Filed: Apr. 10, 2015

(65) Prior Publication Data
US 2015/0239812 A1   Aug. 27, 2015

Related U.S. Application Data

(63) Continuation of application No. PCT/US2013/063968, filed on Oct. 9, 2013, and a
(Continued)

(51) Int. Cl.
C07C 43/04      (2006.01)
C07C 2/00       (2006.01)
(Continued)

(52) U.S. Cl.
CPC ............ C07C 41/06 (2013.01); C07C 1/2074 (2013.01); C07C 43/046 (2013.01); C10L 1/023 (2013.01);
(Continued)

(58) Field of Classification Search
CPC ...... C10L 1/06; C10L 1/10; C10L 2200/0423; C10L 2270/023; C07C 2/00; C07C 43/046
See application file for complete search history.

(56) References Cited

U.S. PATENT DOCUMENTS 3,014,804 A * 12/1961 Els ............................ C12J 1/10
                                                          426/17
4,331,824 A *  5/1982 Ikeda ...................... C07C 1/213
                                                          585/638
(Continued)

FOREIGN PATENT DOCUMENTS

WO   WO-2010064652 A1 *  6/2010  .......... B01J 29/0308

OTHER PUBLICATIONS

Vervecken et al. (Zeolite-induced Selectivity in the Converison of the Lower Aliphatic Carboxylic Acids), 1986, D. Reidel Publishing Company, Chemical Reactions in orgnaic and inorganic Constitued Systems, 95-114 (Year: 1986).*
(Continued)

Primary Examiner — Ellen M McAvoy
Assistant Examiner — Ming Cheung Po
(74) Attorney, Agent, or Firm — William B. Miller

(57) ABSTRACT

Wholly biobased MTBE and ETBE fuel additive materials are described, together with fuel compositions including such additives and processes for making the wholly biobased MTBE and ETBE using isobutene prepared from acetic acid in the presence of a $Zn_xZr_yO_z$ mixed oxide catalyst.

5 Claims, 2 Drawing Sheets

Related U.S. Application Data continuation of application No. PCT/US2013/063971, filed on Oct. 9, 2013, and a continuation of application No. PCT/US2013/062784, filed on Oct. 1, 2013.

(60) Provisional application No. 61/836,188, filed on Jun. 18, 2013, provisional application No. 61/737,312, filed on Dec. 14, 2012, provisional application No. 61/720,433, filed on Oct. 31, 2012.

(51) Int. Cl.
| | | |
|---|---|---|
| *C07C 41/06* | (2006.01) | |
| *C10L 10/10* | (2006.01) | |
| *C10L 1/185* | (2006.01) | |
| *C07C 1/207* | (2006.01) | |
| *C10L 1/02* | (2006.01) | |

(52) U.S. Cl.
CPC ............. *C10L 1/1852* (2013.01); *C10L 10/10* (2013.01); *C07C 2521/06* (2013.01); *C07C 2523/06* (2013.01); *C10L 2200/0423* (2013.01); *C10L 2270/023* (2013.01)

(56) References Cited

U.S. PATENT DOCUMENTS

| | | | | |
|---|---|---|---|---|
| 4,440,963 | A * | 4/1984 | Childs | C07C 41/42 203/67 |
| 4,830,963 | A * | 5/1989 | Brumm | C12P 7/54 435/140 |
| 7,005,541 | B2 * | 2/2006 | Cheung | C07C 51/12 562/519 |
| 9,212,106 | B2 * | 12/2015 | Sun | C07C 1/2074 |
| 9,580,365 | B2 * | 2/2017 | Sun | C07C 1/2078 |
| 9,586,194 | B2 * | 3/2017 | Sun | C07C 5/48 |
| 2013/0210936 | A1 * | 8/2013 | Zhou | C07C 45/41 518/702 |

OTHER PUBLICATIONS

Sun J, Zhu K, Gao F, Wang C, Liu J, Peden CH, Wang Y. .Direct conversion of bio-ethanol to isobutene on nanosized Zn(x)Zr(y)O(z) mixed oxides with balanced acid-base sites.Am Chem Soc. Jul. 27, 2011;133(29) Epub Jul. 1, 2011 (Year: 2011).*

Anthony J. Crisci, Herui Dou, Teerawit Prasomsri, and Yuriy Roman-LeshkovCascade Reactions for the Continuous and Selective Production of Isobutene from Bioderived Acetic Acid Over Zinc-Zirconia Catalysts ACS Catalysis, Oct. 21, 2014 (Year: 2014).*

Junming Sun, Kake Zhu, Feng Gao, Chongmin Wang, Jun Liu, Charles H. F. Peden, Yong Wang, Direct Conversion of Bio-ethanol to Isobutene on Nanosized ZnxZryOz Mixed Oxides with Balanced Acid-Base Sites, Am. Chem. Soc. 2011, 133, 29, 11096-11099 (Year: 2011).*

* cited by examiner

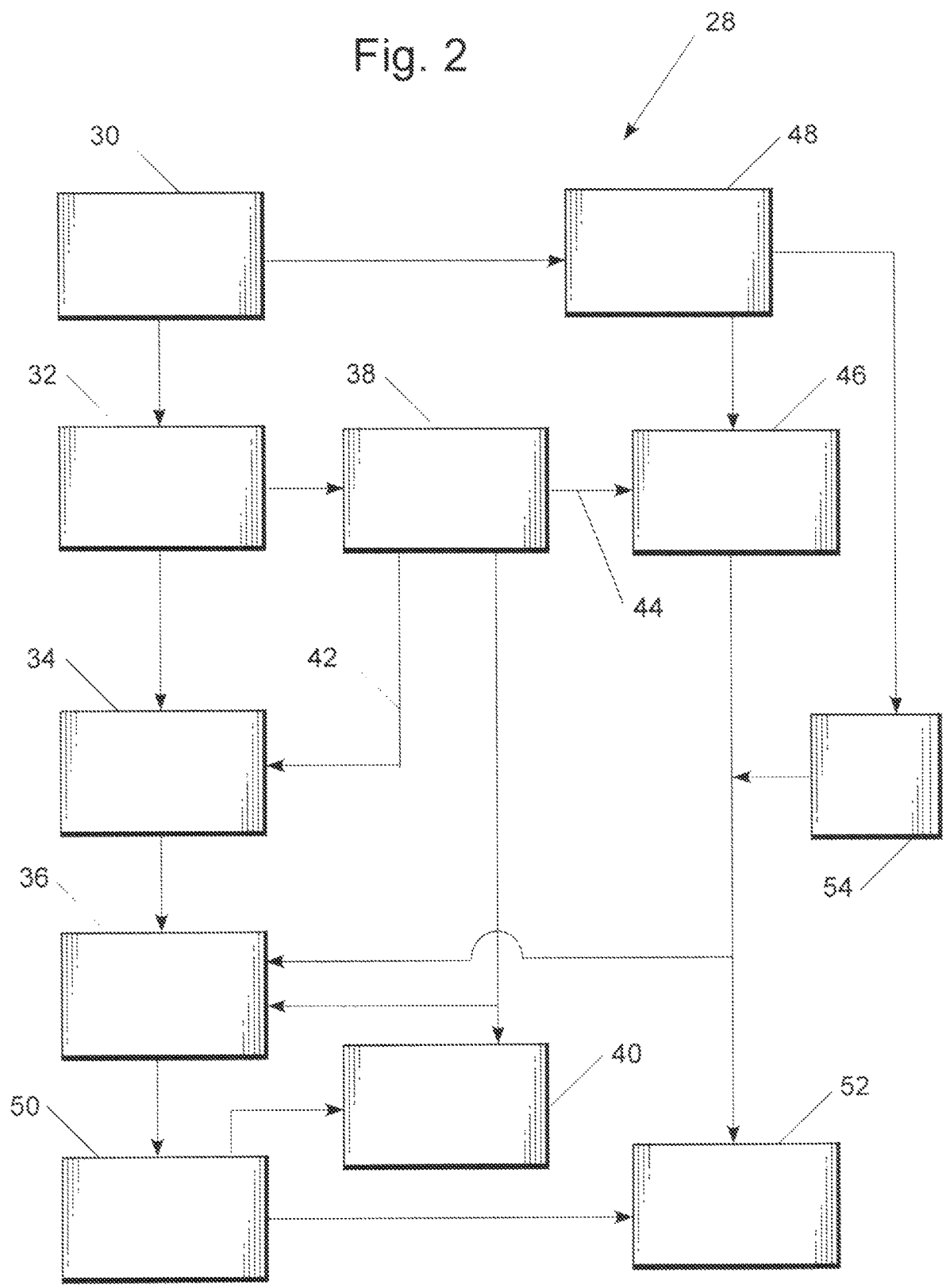

PROCESS FOR MAKING BIOBASED FUEL ADDITIVES

CROSS-REFERENCE TO RELATED APPLICATIONS

The present application is a continuation of International Applications No. PCT/US2013/063971 filed Oct. 9, 2013, now published as WO 2014/204510, which directly claims the benefit of U.S. Provisional Application Ser. No. 61/836,188 filed Jun. 18, 2013; the present application is also a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and, the present application is also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD

The present application relates to processes for making biobased fuel additives, in particular, ethyl and methyl tertiary butyl ethers (ETBE and MTBE, respectively).

BACKGROUND ART

As background, according to Ullman's Encyclopedia of Industrial Chemistry, 12th edition (2012), MTBE was studied extensively in the US during World War II as a high-octane fuel component but was not commercially manufactured until the mid-1970s. With the reduction in the lead content of gasolines at that time, demand for high octane additives increased. Further changes in the composition of gasolines increased demand for MTBE into the late 1990s, but the discovery in subsequent years of MTBE in some groundwater (by virtue of leaking underground storage tanks) has led to a curtailment of MTBE usage in the United States. Still, in Europe as well as in developing parts of the world, MTBE and ETBE remain widely used, commercially important fuel additives.

Conventionally, MTBE has been made in petroleum processing, in integrated processes for the production from a mixed C4 stream from petroleum crackers (after removal of multiply unsaturated hydrocarbons such as butadiene) of isobutene as used in making butyl rubber, polyisobutylene, isobutene oligomers and t-butyl aromatics, of tert-butanol (TBA) and MTBE in desired proportions. The art contains a number of examples of such integrated processes for making non-biobased, conventional MTBE, see, for example, U.S. Pat. No. 4,118,425 to Herbstman, U.S. Pat. No. 4,329,516 to Al-Muddarris, U.S. Pat. No. 4,423,251 to Pujado et al., U.S. Pat. No. 4,981,491 to Harandi et al., and U.S. Pat. No. 5,254,764 to Miracca et al., as well as Ullmann's Encyclopedia of Industrial Chemistry, 11th ed., "Methyl Tert-Butyl Ether", pp 119-130, Wiley-VCH Verlag GmbH & Co. KGaA, Weinheim (2012). The art also contains an example of a more recent integrated process for making isobutene, in part by the dissociation of MTBE formed initially to facilitate the separation of isobutene from the mixed C4 stream, see US 2012/0142985 to Winterberg et al. ETBE for its part has been made in a like manner as MTBE, through using ethanol rather than methanol in the etherification step of such processes.

One of the obvious limitations of current MTBE and ETBE production is the dependence of the known processes for making MTBE and ETBE on petroleum resources and refining for supplying the isobutene to be etherified. In response to recent regulatory and legislative initiatives seeking to encourage the development and commercialization of renewable fuels and renewable source-based fuel additives, an MTBE product ("Bio-MTBE") was launched in October 2012 by Evonik Industries AG that utilizes fossil fuel-derived isobutene with a biobased methanol made from glycerol, ostensibly by the catalytic reforming process described in WO 2010/104467 to Duan et al. ("Duan et al", hereby incorporated by reference). Because glycerol is produced as a co-product of the biodiesel manufacturing process from triglycerides from oilseed crushing, the biobased methanol used by Evonik is said to be considered a waste product under the European Union Renewable Energy Directive, providing added value under the regulatory scheme for meeting EU specifications for biofuel use and $CO_2$ reduction. Ethanol for ETBE, of course, has long been made from grains, yet in regard to Evonik's Bio-MTBE and equally in regard to ETBE by virtue of the isobutene's being derived from petroleum processing there remains an unmet need for wholly biobased MTBE and ETBE fuel additives. The commonly-assigned '433 and '312 applications provide means by which a biobased isobutene may be viably produced, for being combined according to the present invention with a biobased methanol to provide a desired wholly biobased MTBE, or with a biobased ethanol to provide a desired wholly biobased ETBE.

SUMMARY OF THE INVENTION

Thus, in one aspect, the present invention concerns a wholly biobased MTBE fuel additive.

In a second, related aspect, the present invention concerns a wholly biobased ETBE fuel additive.

In still another aspect, a fuel composition is provided which comprises at least one of wholly biobased MTBE and wholly biobased ETBE and which further comprises gasoline.

In a further aspect, a process is described for making a gasoline fuel additive, including the steps of converting acetic acid to isobutene in the presence of a catalyst and under conditions which are effective for carrying out the conversion, and then reacting the isobutene so formed with at least one of methanol and ethanol to form at least one of MTBE and ETBE, respectively.

BRIEF DESCRIPTION OF THE DRAWINGS

FIG. 2 schematically depicts an alternative, biomass-based process embodiment of the present invention for making either or both of MTBE and ETBE using biobased isobutene prepared from acetic acid.

DESCRIPTION OF EMBODIMENTS

Figure 1:
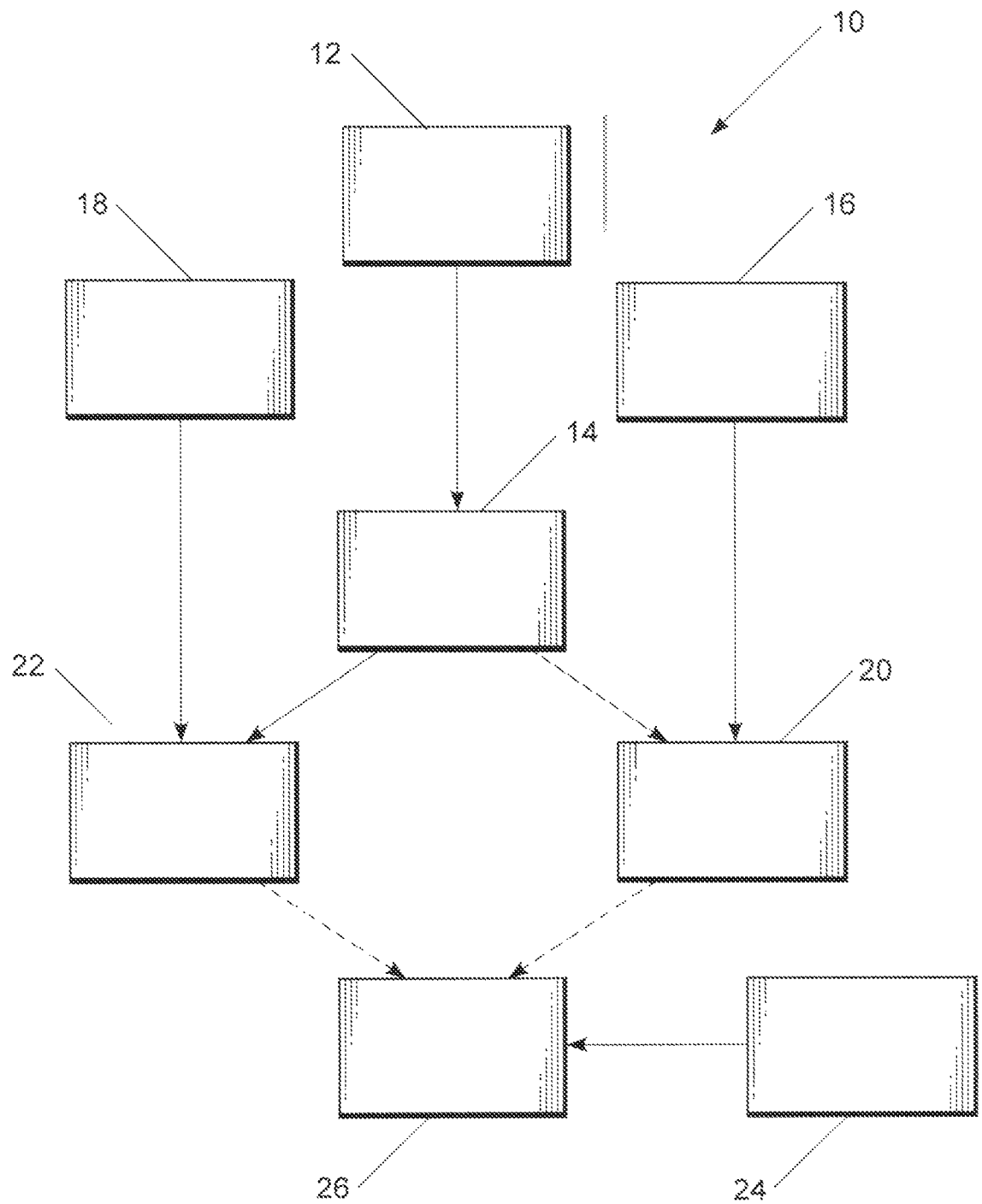
FIG. 1 schematically depicts a process embodiment of the present invention for making either or both of MTBE and ETBE using biobased isobutene prepared from acetic acid.

Referring now to FIG. 1, a process 10 is schematically illustrated wherein acetic acid 12 is converted to isobutene 14 in the presence of a catalyst, particularly, a $Zn_xZr_yO_z$ mixed oxide catalyst, and the isobutene 14 is then combined with at least one of methanol 16 and ethanol 18 to provide the corresponding fuel additive or additives MTBE 20 (from methanol 16 and isobutene 14) and ETBE 22 (from ethanol 18 and isobutene 14), respectively. The MTBE 20 and ETBE 22 fuel additives may be combined with gasoline 24 (CAS 8006-61-9) as is otherwise known to form anti-knock fuel compositions 26 including at least one of MTBE and ETBE, where "gasoline" is conventionally understood as embracing a mixture of volatile hydrocarbons suitable for use in a spark-ignited internal combustion engine and having an octane number of at least 60.

Where the methanol is wholly biobased in origin, being derived from biological carbon sources rather than from methane from natural gas, for example, a wholly biobased MTBE fuel additive may be obtained; ethanol is conventionally derived from biological carbon sources, for example, by fermentation of five- and especially six-carbon sugars, so that with the derivation of the isobutene from acetic acid only (as an alternative to isobutene prepared from such petroleum processing as described above) a wholly-biobased ETBE fuel additive may likewise be obtained.

Parenthetically, by "biobased", we mean those materials whose carbon content is shown by ASTM D6866 to be derived from or based in significant part (at least 20 percent or more) upon biological products or renewable agricultural materials (including but not being limited to plant, animal and marine materials) or forestry materials. "Wholly biobased" thus will be understood as referring to materials whose carbon content by ASTM D6866 is entirely or substantially entirely (for example, 95 percent or more) indicated as of biological origin.

In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

The acetic acid 12 can be obtained by various methods from a number of starting materials, which in turn permits a number of integrated processes to be considered for producing the MTBE 20 and/or ETBE 22 with improved utilization of renewable resources. An example is schematically shown in FIG. 2, discussed more fully below.

For example, acetic acid can be produced from a source of five and six carbon sugars by fermentation. U.S. Pat. Nos. 6,509,180 and 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol, by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as is well known to those skilled in the fermentation art, the fermentation of five and six carbon sugars to form acetic acid can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass, wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. Nos. 4,935,360; 8,236,534; 4,513,084; 4,371,619 and 4,506,012; both one-step fermentation processes from the sugars to acetic acid, acetates or both are disclosed, as well as two-step processes involving a first fermentation to lactic acid (by *lactobacillus* or known methods of homolactic fermentation, preferably) followed by a second fermentation to convert lactic acid to acetic acid, for example, using *Clostridium formicoaceticum*.

Any of the known fermentation methods may, in short, be used to produce acetic acid for conversion to isobutene using our mixed oxide catalysts, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 12 can be made from ethanol, according to any of several known methods employing oxidative fermentation with acetic acid bacteria of the genus *Acetobacter*.

As well or in the alternative, the acetic acid feedstock 12 can be made from methanol through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. Nos. 5,672,743; 5,728,871; 5,773,642; 5,883,289; 5,883,295.

Those skilled in the art will appreciate that making at least a portion of the acetic acid feedstock 12 from methanol may improve the overall carbon efficiency of a process wherein MTBE is a desired product, and similarly, making at least a portion of the acetic acid 12 from ethanol may improve carbon efficiency in a process where ETBE is a desired product.

A non-limiting example of an integrated process 28 for making one or more of the MTBE and ETBE fuel additives from isobutene produced from acetic acid is shown in FIG. 2, though those skilled in the art and familiar with the known processes for producing methanol, ethanol and acetic acid (some of which have been mentioned above or will be mentioned below) and with the known methods by which the "building block" gases carbon dioxide, carbon monoxide and hydrogen may be generated and used to make one or more of the same methanol, ethanol and acetic acid feeds will undoubtedly be able to conceive of a number of other integrated process schemes which all make use of the core acetic acid to isobutene conversion, but differ in the precise manner or extent to which carbon dioxide, carbon monoxide and hydrogen gases are optimally used, for example, integrated process schemes making other products in addition to MTBE and/or ETBE or producing methanol, ethanol or acetic acid in excess of what would be required to make the MTBE and/or ETBE fuel additives.

Turning now to FIG. 2, biomass 30 can be a source of five and six carbon sugars 32, which can undergo a fermentation step 34 as earlier mentioned to make acetic acid 36. Some of the sugars can be fermented according to known methods for fermentation of five- and six-carbon sugars to make ethanol 38, with the ethanol 38 in turn being useful for making ETBE 40 by conventionally practiced etherification process technology and/or for making acetic acid 36 as described above. Carbon dioxide generated as a byproduct in the ethanol fermentation can variously be used as suggested by stream 42 in a homoacetogenic fermentation 34 for making the acetic acid 36, or can be used as suggested by stream 44 to make methanol 46. This carbon dioxide (that is, in streams 42 and 44) can be combined with carbon dioxide from a variety of other sources, for example, with carbon dioxide captured from industrial emissions, generated in the combustion of fossil fuels, sequestered in underground reservoirs or contained in biosynthesis gas 48 from the combustion, gasification or partial oxidation of biomass 30 or of a non-fermentable biomass fraction generated in a fractionation of the biomass 30 to produce fermentable sugars 32. In the context of a biomass fractionation process as described in any of several commonly-assigned applications, namely, published applications WO 2011/097065 and WO 2011/097075 both to Binder et al., as well as Patent Cooperation Treaty Application Ser. No. PCT/US2012/056593, filed Sep. 21, 2012 for "C1-C2 Organic Acid treatment of Lignin Biomass to Produce Acylated Cellulosic Pulp, Hemicellulose, Lignin and Sugars and Fermentation of the Sugars", and PCT/US2012/056593, filed Apr. 10, 2013 for "Liquid-Liquid Separation of Lignocellulosic Biomass to Produce Sugar Syrups and Lignin Fractions", the non-fermentable biomass fraction would include lignin.

In regard to the production of methanol 46, with increasing concerns for the abatement of greenhouse gases such as carbon dioxide in recent years, a substantial amount of work has been reported on methods to convert carbon dioxide to methanol, see, for example, Wesselbaum et al., "Hydrogenation of Carbon Dioxide to Methanol by Using a Homogeneous Ruthenium-Phosphine Catalyst", *Angew. Chem. Int. Ed.*, vol. 51, pp 7499-7502 (2012); Ma et al., "A Short Review of Catalysis for $CO_2$ Conversion", *Catalysis Today*, vol. 148, pp 221-231 (2009); Borodko et al., "Catalytic Hydrogenation of Carbon Oxides—a 10-Year Perspective", *Applied Catalysis A: General*, vol. 186, pp 355-362 (1999); and U.S. Pat. No. 8,212,088 to Olah et al., "Efficient and Selective Chemical Recycling of Carbon Dioxide to Methanol, Dimethyl Ether and Derived Products" and the various additional references cited in each of these. Those skilled in the art will thus be well-acquainted with processes and associated catalysts for producing methanol 46 from carbon dioxide in stream 44 and from carbon dioxide, carbon monoxide and hydrogen derived from the biomass 30 (or from a biomass fraction obtained from fractionation of biomass 30) and found in biosynthesis gas 48, though it will be appreciated that methanol 46 or these "building block" gases can alternately or additionally be obtained from a biomass 30 by anaerobic digestion through methane, from electrolysis of water using energy from geothermal sources, by electrolytic cleavage of carbon dioxide to produce carbon monoxide and water and so forth. As well, it will be appreciated that the methanol used for forming MTBE with the biobased isobutene could be prepared from methane from natural gas, but preferably a substantial proportion and more preferably all of the methanol used in the inventive process will be wholly biobased as suggested in FIG. 2.

The methanol 46 can, as indicated in FIG. 2 and as just mentioned, be combined with biobased isobutene 50 (from acetic acid 36) for forming the MTBE fuel additive 52, and in another embodiment can be combined with carbon monoxide 54 from biosynthesis gas 48 (or from the electrolytic cleavage of $CO_2$ from any of the sources mentioned above in connection with the generation of the methanol 46) to produce acetic acid 36.

The acetic acid 36 is converted to isobutene 50, preferably using a $Zn_xZr_yO_z$ mixed oxide catalyst. In one embodiment, the $Zn_xZr_yO_z$ mixed oxide catalyst can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yO_z$ mixed oxide catalysts made by a hard template method are further described in Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp 11096-11099 (2011), along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from 1:100 to 10:1, preferably from 1:30 to 1:1, especially 1:20 to 1:5, and still more preferably 1:12 to 1:10.

Parenthetically, in the present application where any range of values is given for any aspect or feature of the catalysts of the present invention or any process described for using the catalysts of the present invention, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the alternative, incipient wetness method are consistent in their particle size with the catalysts described in the Jacobsen et al. article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than 0.14 percent by weight of sulfur. In our '433 application, it was reported in this regard that catalysts made by the incipient wetness method would desirably be substantially sulfur-free, preferably including less than 0.01 percent by weight of sulfur and more preferably including less than 0.001 weight percent of sulfur. It was postulated that the reduced sulfur content enabled by the incipient wetness method as compared to the hard template method contributed significantly to the much improved stability observed for the incipient wetness method catalysts of the '433 application for the ethanol to isobutene process.

In the context of a process for converting acetic acid to isobutene, however, in at least some embodiments and under certain process conditions some sulfur does appear to be beneficial, though as just indicated, it is expected that the amount of sulfur will preferably be such that the catalysts are characterized as low sulfur catalysts. Such low sulfur catalysts are most readily made by the incipient wetness method described briefly above.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. Low sulfur catalysts can also be made by the incipient wetness method starting with zinc and zirconium compounds that are sulfur-free or substantially sulfur-free, then doping in a desired sulfur content into the $Zn_xZr_yO_z$ mixed oxide catalysts.

The conditions and times for the drying and calcining steps of an incipient wetness preparation will depend, of course, on the particular zinc and zirconium materials and solvent used, but in general terms, the drying step can be accomplished in a temperature range of from 60 degrees Celsius to 200 degrees Celsius over at least 3 hours, while the calcining can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, low sulfur catalysts as described could be prepared by a hard template method as described in the Jacobsen et al. publication, except that a suitably very low sulfur content carbon is used for the hard template to realize a low sulfur content in the finished catalyst.

In certain embodiments, the acetic acid to isobutene process can be conducted continuously in the gas phase, using a fixed bed reactor or flow bed reactor. The reaction temperature may be in a range from 350 to 700 degrees Celsius, preferably, in a range from 400 to 500 degrees Celsius, and the WHSV can be in a range from 0.01 $hr^{-1}$ to 10 $hr^{-1}$, preferably from 0.05 $hr^{-1}$ to 2 $hr^{-1}$. Acetic acid/water solutions with steam to carbon ratios from 0 to 20, preferably from 2 to 5, can be used to provide acetic acid to the catalyst. An inert carrier gas such as nitrogen can also be used.

The present invention is further illustrated by the following non-limiting examples:

Example 1

Commercial zirconium hydroxide was dried at 120 degrees Celsius for more than 5 hours. Calculated amounts of $Zn(NO_3)_2$ (from Sigma-Aldrich, more than 99.8 percent purity) were dissolved in water to form a series of clear solutions. Dried zirconium hydroxide (also from Sigma-Aldrich, more than 99.8 percent purity) was then mixed with the solutions in turn by incipient wetness, in order to form wet powders impregnated with Zn in certain proportions to the zirconium in the form of the dried zirconium hydroxide powder. The wetted powders were then dried at 80 degrees Celsius for 4 hours, followed by calcination at 400 degrees Celsius for 2 hours and at 600 degrees Celsius for 3 hours to obtain a series of $Zn_xZr_yO_z$ catalysts.

Ethanol to isobutene runs were conducted with the catalysts thus prepared in a fixed-bed stainless steel reactor, having an inside diameter of 5 millimeters. A given amount of catalyst was packed between quartz wool beds. A thermocouple was placed in the middle of the catalyst bed to monitor the reaction temperatures. Before beginning the reaction, the catalyst beds were first pretreated by flowing 50 ml/minute of nitrogen at 450 degrees Celsius through the catalyst over a half hour, then a mixture of ethanol/water at steam to carbon ratios from 1 to 5 was introduced into an evaporator at 180 degrees Celsius by means of a syringe pump and carried into the reactor by the flowing nitrogen carrier gas. Meanwhile, the product line was heated to in excess of 150 degrees Celsius before a cold trap, to avoid condensing the liquid products in the product line.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

An ethanol/water solution (steam to carbon ratio of 2.5) was then supplied by flowing N2 to the reactor at a weight hourly space velocity (WHSV) of 0.95 $hr^{-1}$. The ethanol concentration was 15.1 percent by weight, and the reaction temperature was 450 degrees Celsius. Ethanol conversion was 100% throughout, and isobutene selectivity declined by less than 2 percent over 200 hours on stream for the series of catalysts prepared as described.

Thermogravimetric and differential scanning calorimetry analysis of the recovered, spent catalysts showed only about 0.7 weight percent of coke after 207 hours onstream.

Example 2

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst.

An acetic acid to isobutene process was conducted with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 percent by weight of methane, about 10 percent by weight of acetone, about 33 percent by weight of carbon dioxide and more than about 50 percent by weight of the desired isobutene product was obtained; in contrast to the ethanol to isobutene process using these same $Zn_xZr_yO_z$ mixed oxide catalysts in Example 1, no ethylene or propylene was produced. The catalyst showed very high stability over the full duration of the run, with no signs of observable deactivation after more than 1400 minutes of time-on-stream operation.

Examples 3 Through 11

For these examples, additional $Zn_xZr_yO_z$ mixed oxide catalysts were prepared both by the incipient wetness method used in Example 1 (1W in Table 1 below) but also by the prior art hard template method (HT), and these were evaluated for the acetic acid to isobutene conversion and the products were analyzed using the same apparatus and method described in Example 2, but under different sets of reaction conditions (as summarized in Table 1 below).

TABLE 1

Further Acetic acid to Isobutene Examples

| Ex # | Catalyst | Zn/Zr ratio | Reaction temp. (° C.) | WHSV ($g_{acetic}$/$g_{catal}$/hr) | Steam to carbon ratio | $C_{G\text{-}aceticacid}$ (wt %) | Acetone selectivity (mol %) | Isobutene selectivity (mol %) |
|---|---|---|---|---|---|---|---|---|
| 3 | HT | 1/15 | 450 | 0.25 | 5 | 1.3 | 30.5 | 41.7 |
| 4 | HT | 1/15 | 450 | 1.14 | 5 | 1.5 | 61.1 | 18.4 |
| 5 | IW | 1/8 | 415 | 0.1 | 5 | 1.4 | 9.8 | 52.5 |
| 6 | IW | 1/10 | 415 | 0.95 | 5 | 22.3 | 50.8 | 20.1 |
| 7 | IW | 1/10 | 450 | 0.16 | 2.5 | 18.8 | 0.7 | 50.6 |
| 8 | IW | 1/10 | 450 | 0.65 | 2.5 | 18.8 | 8.3 | 46.9 |
| 9 | IW | 1/10 | 415 | 0.16 | 2.5 | 18.8 | 5.7 | 57.2 |
| 10 | IW | 1/10 | 415 | 0.33 | 2.5 | 18.8 | 16.4 | 45.3 |
| 11 | IW | 1/10 | 415 | 0.65 | 2.5 | 18.8 | 30.5 | 35.0 |

The invention claimed is:

1. A process for making a gasoline fuel additive, comprising:
   converting acetic acid to isobutene in the presence of a catalyst; and
   reacting the isobutene with at least one of methanol and ethanol, wherein the catalyst for converting the acetic acid to isobutene is a $Zn_xZr_yO_z$ mixed oxide catalyst, wherein the ratio of x:y is from 1:100 to 10:1 and z is a stoichiometric integer for the mixed oxide catalyst.

2. A process as in claim 1, wherein the catalyst for converting the acetic acid to isobutene contains less than 0.14 percent by weight of sulfur.

3. A process as in claim 2, wherein the catalyst contains less than 0.01 percent by weight of sulfur.

4. A process as in claim 3, wherein the catalyst contains less than 0.001 percent by weight of sulfur.

5. A process as in claim 1, wherein x:y is from 1:12 to 1:10.

\* \* \* \* \*